US012790579B2

(12) United States Patent

Laurent et al.

(10) Patent No.: US 12,790,579 B2

(45) Date of Patent: Nov. 10, 2026

(54) DEVICE FOR HOMOGENIZATION OF A MULTICOMPONENT FLUID

(71) Applicant: ASTRAVEUS, Paris (FR)

(72) Inventors: Jérémie Laurent, Villeurbanne (FR); Giulia Ghinatti, Rovigo (IT); Vincent Thisse, Choisy-le-Roi (FR); Xue Hou, Suresnes (FR)

(73) Assignee: ASTRAVEUS, Paris (FR)

( * ) Notice: Subject to any disclaimer, the term of this patent is extended or adjusted under 35 U.S.C. 154(b) by 892 days.

(21) Appl. No.: 18/002,707

(22) PCT Filed: Jun. 22, 2021

(86) PCT No.: PCT/EP2021/067043

§ 371 (c)(1),
(2) Date: Dec. 21, 2022

(87) PCT Pub. No.: WO2021/259955

PCT Pub. Date: Dec. 30, 2021

(65) Prior Publication Data

US 2023/0235270 A1 Jul. 27, 2023

(30) Foreign Application Priority Data

Jun. 26, 2020 (EP) .................................... 20305713

(51) Int. Cl.

*C12M 1/00* (2006.01)
*C12M 1/26* (2006.01)

(Continued)

(52) U.S. Cl.

CPC ............ *C12M 47/08* (2013.01); *C12M 23/16* (2013.01); *C12M 23/40* (2013.01); *C12M 33/12* (2013.01); *C12M 41/40* (2013.01)

(58) Field of Classification Search

CPC .............................. C12M 23/16; C12M 47/08

See application file for complete search history.

(56) References Cited

U.S. PATENT DOCUMENTS

| | | | |
|---|---|---|---|
| 2001/0017815 A1 | 8/2001 | Ackermann et al. | |
| 2018/0079998 A1 | 3/2018 | Jones et al. | |

FOREIGN PATENT DOCUMENTS

| | | | |
|---|---|---|---|
| CN | 201476419 U | 5/2010 | |
| CN | 110325841 A * | 10/2019 | ............ G01N 33/02 |

(Continued)

OTHER PUBLICATIONS

International Search Report issued Sep. 16, 2021, in corresponding International Patent Application No. PCT/EP2021/067043, 3 pages.

*Primary Examiner* — Michael A Marcheschi
*Assistant Examiner* — Jonathan E Lepage
(74) *Attorney, Agent, or Firm* — Maier & Maier, PLLC

(57) ABSTRACT

A device for homogenizing a multicomponent fluid including a main channel, a first and a second buffer channels, a collector connected to the main channel with a main conduct, to the first buffer channel with a first fiber and to the second buffer channel with a second fiber. The collector further includes a flow separation point aimed at dividing the main conduct into the first and second fibers, a pumping unit configured to move the multicomponent fluid from the main channel to the first or the second buffer channels through the collector and move the multicomponent fluid from the first or the second buffer channels to the main channel through the collector.

14 Claims, 9 Drawing Sheets

(51) Int. Cl.
*C12M 1/34* (2006.01)
*C12M 3/06* (2006.01)

(56) References Cited

FOREIGN PATENT DOCUMENTS

| | | | | | |
|---|---|---|---|---|---|
| DE | 20209547 | U1 * | 9/2002 | ............ | C12M 45/02 |
| WO | 2005089928 | A1 | 9/2005 | | |
| WO | 2018016622 | A1 | 1/2018 | | |
| WO | WO-2019126212 | A1 * | 6/2019 | ............ | C12M 35/04 |

* cited by examiner

DEVICE FOR HOMOGENIZATION OF A MULTICOMPONENT FLUID

FIELD

The present invention relates to a device and a method for handling a particle suspension, in particular a cell suspension.

BACKGROUND

Multicomponent fluids such as emulsions and particle suspensions are frequently handled in many industries including chemical industries, cosmetic industries, bioindustries and in particular the biopharmaceutical industries.

The handling of multicomponent fluids is typically made difficult by the fact that the different components of the fluid are not subjected to identical forces per unit mass during the flow and between flow operations. The magnitude of hydrophobic forces, electrostatic forces, inertial forces, sedimentation forces, among others, per unit mass typically differ between the components of a particle suspension or an emulsion, for example. This results in the flow acting and transporting the different components of the multicomponent fluid in different ways which typically decreases the fluid homogeneity. A typical example is when sedimentation forces lead to particles of a suspension being displaced much more slowly than the fluid in average.

In the industry homogenization of a multicomponent fluid is typically sought by mixing with vorticial flow, often using a rotor immersed in the fluid, or rolling or shaking of the container. These approaches have important limitations and are generally not suitable to reach high homogeneity, to handle very sensitive fluids, and to handle small volumes. Notable inconvenient of these approaches are the following:

- they may cause damages to components of the fluid or more generally alter its properties, in particular in the case of the use of rotors,
- they are less effective or ineffective for small liquid volumes due to the fact that increasing viscous effects in reduced volumes reduce the ratio between the volume lateral dimension and the smallest vortex size (Kolmogorov length), which corresponds to less fluid brewing, while fluid sensitivity may limit the allowable intensity of the mixing and the minimal allowable Kolmogorov length to avoid excessive damages,
- they are more difficult, and sometimes impossible, to integrate to single use closed processing systems, and in particular small volume closed single use systems, which are of particular interest in the biopharmaceutical industry and for the handling of high activity products,
- finally, they may, paradoxically, generate heterogeneity because the flow patterns they generate may lead to effects concentrating some components of the fluid in specific parts of the volumes. For example, inertial lift forces typically drive particles of a particle suspension laterally away from velocity maxima in a flow cross section. as a result, even after long periods of mixing important heterogeneity may remain despite fluid brewing. To illustrate this point, it is typical to obtain variability of cell concentration within a cell suspension immediately after the use of a "vortex" shaker higher than 30%.

Other types of devices including microfluidic devices provide mixing using channel geometries that induce vortices in the fluid flow. These devices however provide only local mixing and not over the longitudinal extension of the fluid volume. Although loop flow in circuits comprising such mixers using miniature peristaltic pumps has been proposed this approach is not convenient, notably because it handles a volume fixed by the characteristics of the device used for this method.

German Utility Model DE20209547 discloses a device for homogenizing a cell suspension. Mixing is obtained by use of a spheric obstacle located in the flow—thus inducing shear—when the cell suspension is transferred from one syringe to another syringe. However, flow is not divided into two separate tanks.

International patent application WO2005/089928 discloses a kit for preparation of coated particles using a t-shaped junction to make a contact between particles and coating material—a lipid here.

International patent application WO2018016622 discloses a mixing device using a T-shaped junction allowing to combine to different liquids.

These disclosures, as well as other known elements such as microfluidic chaotic mixers, provide a lateral mixing, i.e. mixing of fluid in the vicinity of the cross-section plane. They do not provide longitudinal mixing while the longitudinal direction is in such cases the largest ones and while longitudinal heterogeneity is the most impactful, e.g. in dosing applications. As a result, they do not produce a complete homogenization nor a homogeneity in the perspective of dosing applications.

Obtaining and maintaining the homogeneity of a multicomponent fluid is essential in many use cases in the above-mentioned industries. In particular the multicomponent fluids are very often used to transfer and dose one of its components, the dosage being often derived from the displaced fluid volume and the component average concentration in the fluid. Thus, the lack of homogeneity of multicomponent fluids leads to inaccurate dosing. Because the dosed subcomponents of a multicomponent fluid are often reactive elements, such as catalysts, radioelements or living cells, underdosing and overdosing of these subcomponents due to the lack of homogeneity of the fluid can lead to very serious consequences from performance losses or batch losses to potentially deadly accidents.

High efficiency homogenization and dosing system for multicomponent fluids, and in particular for sensitive fluids and/or small volume applications, would therefore solve an important technical problem faced by many industries.

It is this technical need that the invention is intended to fulfill, in particular for the handling of particle suspensions, by proposing a device and method for homogenizing and dosing a multicomponent fluid such as an emulsion or a particle suspension, in particular a cell suspension, and a method of using the same.

SUMMARY

For this purpose, a first subject of the invention is a device for homogenizing a multicomponent fluid, in particular a cell suspension, comprising:

i. a main channel, ii. at first and a second buffer channels, iii. a collector connected to the main channel by means of a main conduct, and connected to the first buffer channel by means of a first fiber and to the second buffer channel by means of a second fiber, said collector further comprising a flow separation point aimed at dividing the main conduct into the first and second fibers, iv. a pumping unit and a control unit configured to:
  move the multicomponent fluid from the main channel to the first or the second buffer channels through the collector, and
  move the multicomponent fluid from the first or the second buffer channels to the main channel through the collector.

The device according to the invention may comprise one or several of the following features, taken one by one or combined with others:
- the pumping unit may comprise at least one sensor allowing the detection of fluid, inside one of the channels, the main conduct, the fibers or the collector,
- one sensor may be positioned, on each fiber, between the flow separation point and each buffer channel,
- each sensor is able to detect the presence of a fluid without direct contact to the fluid,
- each sensor situated on a fiber may be situated at a distance inferior to 20 cm from flow separation point, and more preferably at a distance inferior to 10 cm from the flow separation point,
- the pumping unit may comprise at least one volumetric pump in order to move a determined multicomponent fluid volume from the first or second buffer channels to the main channel or from the main channel to the first or second buffer channels,
- the pumping unit may comprise at least one servo pump being controlled with a feedback loop activated by the at least one sensor.

Another object of the invention is a system for processing a multicomponent fluid comprising:

i. at least four bioprocessing microfluidic devices;
ii. at least three reservoirs or ports configured to connect a reservoir;
iii. at least one buffer tank; and
iv. at least two fluidic connection systems;

wherein the first fluidic connection system comprises valves and connecting means between valves, so that each reservoir or port configured to connect a reservoir may be in fluidic connection with each buffer tank; and the second fluidic connection system comprises valves and connecting means between valves, so that each bioprocessing microfluidic device may be in fluidic connection with each buffer tank; and wherein one of the at least one buffer tank is the device for homogenizing a multicomponent fluid disclosed hereabove.

A further object of the invention is a method for homogenizing a multicomponent fluid, in particular a cell suspension, comprising:

a. defining a homogenizing parameter n, which is an integer larger than or equal to 2;
b. providing a device comprising:
  i. main channel,
  ii. n buffer channels,
  iii. a collector connected to the main channel by means of a main conduct, and connected to each of the n buffer channels by means of a fiber, said collector further comprising a flow separation point aimed at dividing the main conduct into at least two subsets of the n fibers, and
  iv. a pumping unit configured to
    move the multicomponent fluid from the main channel to the buffer channels through the collector, or
    move the multicomponent fluid from the buffer channels to the main channel through the collector,
c. filling the collector and the main channel at least partially with multicomponent fluid,
d. flowing successively, through the flow separation point of the collector, a fraction of the volume of the multicomponent fluid from the main channel to each buffer channels in such a way that, after step d is finished, the portion of residual fluid volume situated upstream the flow separation point is inferior to 20% of the volume, and
e. flowing simultaneously the multicomponent fluid from all buffer channels to the main channel.

The method according to the invention may comprise one or several of the following steps, taken one by one or combined with others:
- the fraction of the volume of multicomponent fluid which is successively flown to the buffer channels may be equal to 1/n,
- the portion of residual fluid volume situated upstream the flow separation point may be inferior to 10% of the volume,
- the portion of residual fluid volume situated upstream the flow separation point may be inferior to 5% of the volume,
- steps d and e may be repeated at least twice,
- each time step d is repeated, the filling order of volume of the buffer channels or fraction of volume flown in the buffer channels may be modified.

DETAILED DESCRIPTION

Device

Figure 1:
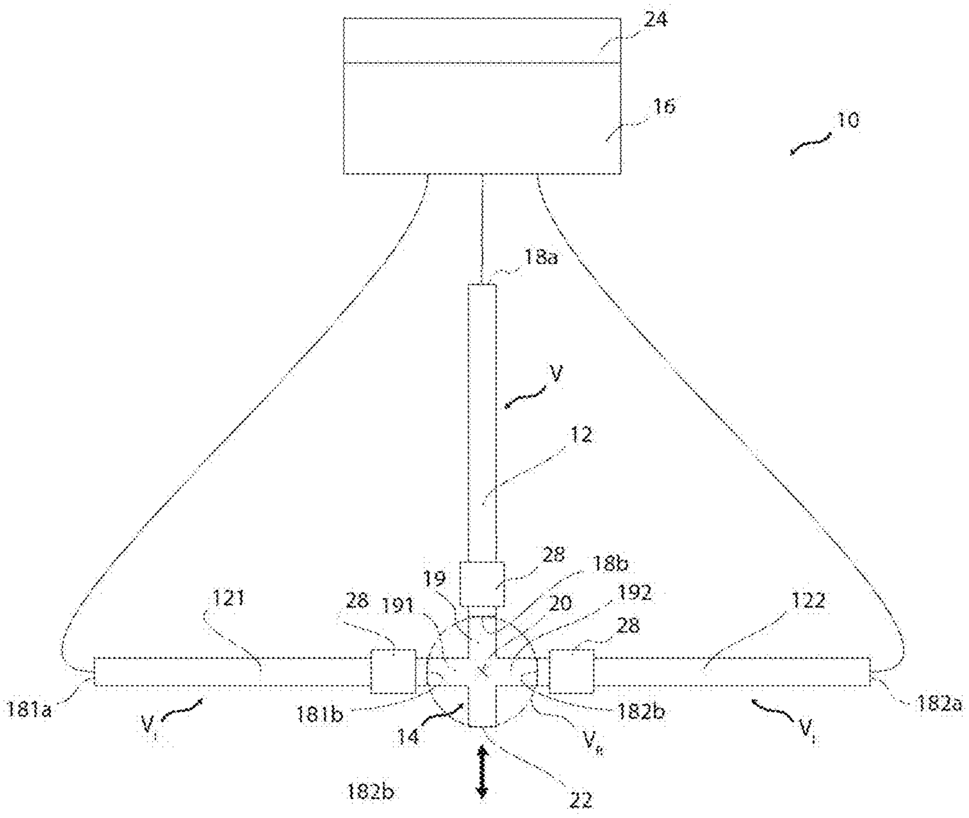
FIG. 1 is a schematic cross-sectional view of a first embodiment of the device according to the invention.
Figure 2:
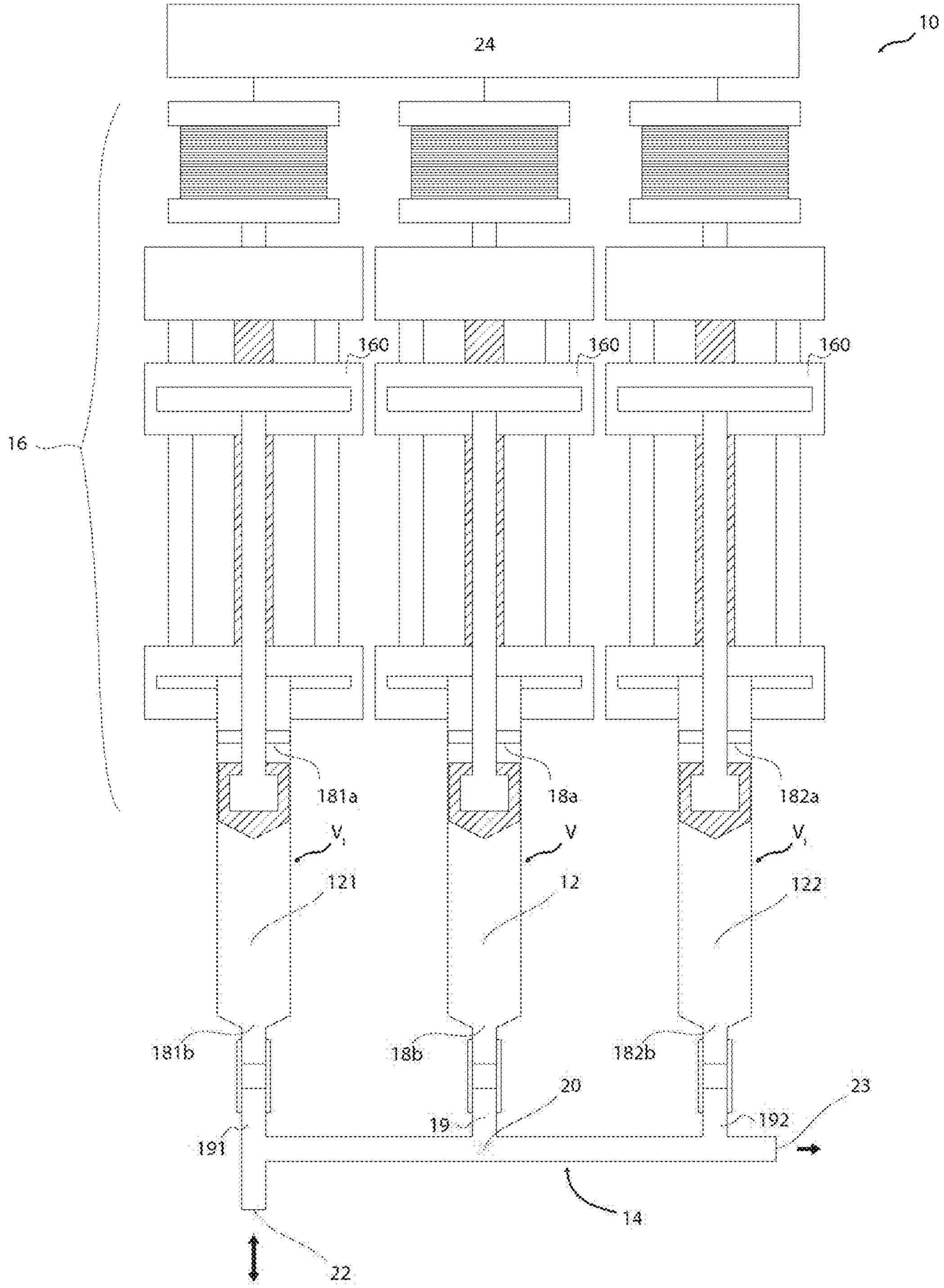
FIG. 2 is a schematic cross-sectional view of a second embodiment of the device according to the invention.
Figure 3:
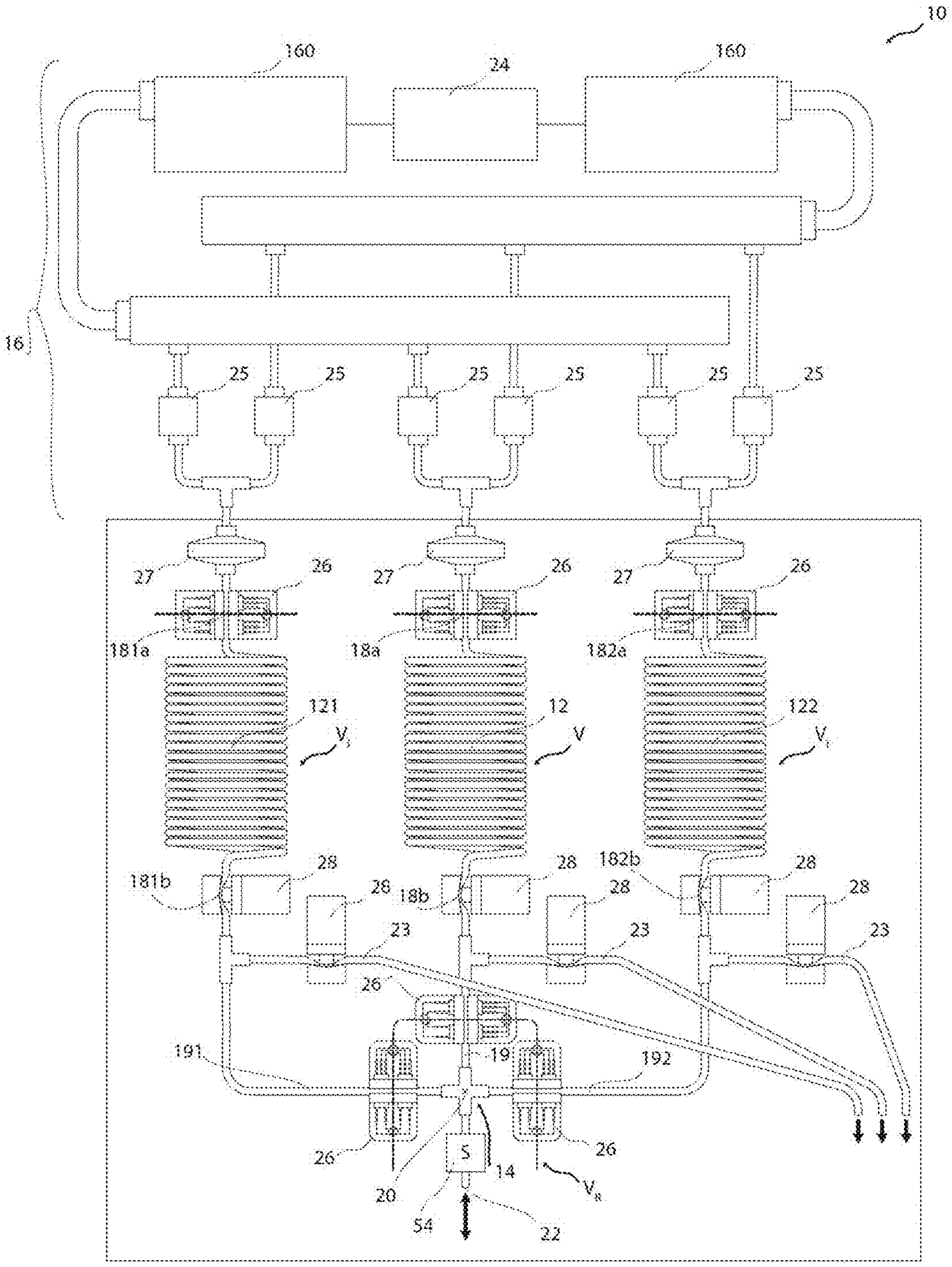
FIG. 3 is a schematic cross-sectional view of a third embodiment of the device according to the invention.

As can be seen on FIGS. 1, 2 and 3 the device 10 for homogenizing a multicomponent fluid according to the invention comprises:
- a main channel 12;
- a first and a second buffer channels 121, 122,
- a collector 14,
- a pumping unit 16.

In the present specification, a multicomponent fluid designates a fluid displaying a condensed phase susceptible to viscous flow in which one or more particle types, for example cells, are in suspension or dispersed. To simplify it will be talked, in the present specification, about particles in suspension, but it is to be understood that the particles may be partly dispersed and for example sedimented or aggregated in certain cases, although the present invention generally aims at avoiding sedimentation, aggregation or coalescence effects. Particles in suspension may have any shape and composition, they may be for example gas bubbles, liquid droplets, gel droplets, solid particles or microparts, living cells, enucleated cells, cell aggregates, organoids, multicomponent particles, hollow particles, non-imitatively. Some particles of the suspension may be stable over the handling procedure duration, but some may also be reactive with components of the multicomponent fluid or incident elements such as gas permeated through device walls, catalyst present at the device walls, energy for example in the form or electromagnetic or mechanical wave transmitted by device walls—non-limitative—in which cases the invention may be used to perform reactions in the multicomponent fluid while maintaining its homogeneity.

In some further embodiment not shown, the device 10 can comprise an unlimited amount of buffer channels.

The main channel 12 works as a reservoir and aims at storing the multicomponent fluid, in particular a cell suspension, to be homogenized. This main channel 12 can display any suitable shape for a reservoir, as can be seen on the different embodiments illustrated on FIGS. 1, 2 and 3. Generally speaking, the main channel 12 comprises an inlet 18*a* and an outlet 18*b*. More specifically, the device 10 according to the embodiment illustrated on FIG. 3 comprises a main channel 12 having an inner volume $V_{mc}$ and a length L of its longitudinal fiber. At one end, the channel 12 is terminated by an inlet 18*a*, and at its other end, the channel 12 is terminated by an outlet 18*b*. The main channel 12 has an internal cross-section of inner surface area $S_{mc}$ lower than 9 mm$^2$, an inner diameter D corresponding to the largest distance between two points in the same cross section, and a dimension H calculated as S/D. In some embodiments, the main channel 12 is a cylindrical tube with an inner diameter D between 0.1 mm and 3.4 mm, preferably between 0.2 mm and 2 mm. In some embodiments the main channel volume $V_{mc}$ is comprised between 10 μL and 100 mL, preferably between 20 μL and 50 mL, and more preferably between 50 μL and 20 mL. In some embodiments, the buffer channels volumes are similar and close to or greater than half the main channel volume $V_{mc}$, unless the number of buffer channels 121, 122 is greater than two, in which case the buffer channels volumes are preferably similar and close to or greater than 1/n times the main channel volume $V_{mc}$. In the embodiment shown in FIG. 3, the channel 12 of the device 10 exhibits a compacted coiled structure, so that its length L is much greater, i.e. at least twice greater, than the largest distance between two points of the main channel 12 volume. The compaction of the main channel 12 is necessary for the ergonomics. Indeed, the channel length L is typically large compared to, for example, the dimension of the hands of an operator. The compaction of the main channel 12 also reduces the risk of entanglement or collision. Preferably, radius of curvature of the main channel 12 along its longitudinal direction is larger than 3 times the inner diameter D of the main channel 12. More preferably, the radius of curvature of the main channel 12 along its longitudinal direction is larger than 5 times the inner diameter D of the main channel 12. This reduces risks of centrifugal effects in the channel interfering with the device 10 functions. The inlet 18*a* is connected to the pumping unit and the outlet 18*b* is connected to the collector 14.

The first and second buffer channels 121, 122 display a similar shape than the main channel 12. Each of the buffer channels 121, 122 comprises an inlet 181*a*, 182*a* and an outlet 181*b*, 182*b*. The inlets 181*a*, 182*a* are connected to the pumping unit 16. The outlets 181*b*, 182*b* are connected to the collector 14. In some embodiments the inlet 18*a* or the inlets 181*a* and 182*a* are connected to the pumping unit 16.

In the embodiments illustrated on FIGS. 1, 2 and 3, the collector comprises three inlets each inlet being connected to one of the outlets 18*b*, 181*b*, 182*b* of each channel 12, 121, 122. In some further embodiments, not shown, in which the device comprises more than two buffer channels, the collector 14 comprises as many inlets as necessary to connect the main buffer 12 and each of the buffer channels. More precisely, in the embodiments of FIGS. 1, 2 and 3, the collector 14 is connected to the outlet 18*b* of the main channel 12 by means of a main conduct 19. The collector 14 is connected to the outlet 181*b* of the first buffer channel 121 by means of a first fiber 191 and to the outlet 182*b* of the second buffer channel 122 by means of a second fiber 192. In alternative embodiments comprising more than two buffer channels, there are as many fibers as buffer channels.

The average cross-section of the main channel 12, the first and second buffer channels 121, 122, the main conduct 19, and the first and second fibers 191, 192 is comprised between 0.1 mm$^2$ and 90 mm$^2$. More precisely, the average cross-section of the main channel 12, the first and second buffer channels 121, 122, the main conduct 19 and the first and second fibers 191, 192 is comprised between 0.1 mm$^2$ and 9 mm$^2$.

The main channel 12, the main conduct 19, and the first and second fibers 191, 192 each display a standard hydraulic resistance of less than $10^{13}$ Pa·s/m$^3$. More precisely, the main channel 12, the main conduct 19, the first and second fibers 191 192 each displays a standard hydraulic resistance of less than $10^{13}$ Pa·s/m$^3$.

By "standard hydraulic resistance", it is meant the hydraulic resistance of the considered fluidic element for a flow of water at 20° C., under atmospheric pressure (1 bar), measured at a flow rate of 10 μL/s. It is defined as the ratio between the pressure difference along a section of the fluidic element and the flow rate through the same fluidic element. For a cylindrical channel in laminar flow and according to Poiseuille law, hydraulic resistance writes:

$$R_h = \frac{8\mu L}{\pi R^4},$$

where μ is the dynamic viscosity, L and R are the length and radius of the cylindrical channel Hydraulic resistance is an intrinsic characteristic of a fluidic element, completely defined by its geometry for a given fluid and in laminar flow conditions.

The collector 14 further comprises a flow separation point 20 aimed at dividing the main conduct 19 into the first and second fibers 191, 192. In case there are more than two buffer channels, for example n buffer channels, the collector 14 connects the main channel 12 to each of the n buffer channels by means of a fiber, and said collector further comprises a flow separation point 20 aimed at dividing the main conduct 19 into at least two subsets of the n fibers.

In other words, the flow separation point 20 is the point situated the closest to both the first and second fibers 191 and 192.

The flow separation point 20 can be estimated as being the center of the largest convex volume defined as the union of the main conduct 191 and the first and second fibers 191, 192 sub volumes; or more roughly, as the center of the largest sphere entirely included in the volumes of the main conduct 19, and the first and second fibers 191, 192 with roughly equal portions of this sphere included in each of the main conduct and first and second fibers volumes (see FIG. 3).

The collector 14 may form one piece with the main conduct 19 and first and second fibers 191, 192.

The volume of the collector 14 is either part of or equal to a residual volume $V_R$. This residual volume $V_R$ corresponds to the volume of multicomponent fluid which is not homogenized and will be detailed further below. In cases where the collector 14 defines a residual volume $V_R$, the collector 14 and the residual volume $V_R$ are defined by the pumping limits of the pumping unit 16. In the particular case of the embodiment of FIG. 2, this volume corresponds to the inner volume which can not be swiped by the syringe pump piston-gasket assembly.

The device 10 also comprises a collector inlet/outlet 22 used to input or recollect the multicomponent fluid after homogenization. The collector inlet/outlet 22 is preferably connected to the collector 14 close to the separation point 20. The collector outlet 22 may alternatively be connected to any one of the channels 12, 121, 122, preferably close to the flow separation point 20.

The device 10 may also comprise a quality sensor S situated downstream the collector inlet/outlet 22, said quality sensor S aimed at analyzing fluidic properties of a fluid flowing through the channels 12, 121, 122 or the collector 14.

In FIGS. 1 and 3, the collector displays a general cross shape, connecting the first and second fibers 191, 192 with a 180° angle and the main conduct with a 90° angle to each fiber 191, 192. The collector inlet/outlet 22 is connected with a 180° angle to the main conduct 19 and a 90° angle to each fiber 191, 191.

In some embodiments, the channels 12, 121, 122 and the collector 14 are part of a replaceable sterilized assembly.

In some embodiments, the main channel 12 and the buffer channels 121, 122 may be equipped with a purge outlet 23 preferably located close to the corresponding channel outlet (i.e. connection site with the collector). In preferred embodiments, each of the main channel 12 and buffer channels 121, 122 is equipped with a purge outlet 23 regulated by a valve 28. Purge outlets 23 allow to flush away residual fluids in the collector 14 and eventually part of the fluid remaining in the main and buffer channels 12, 121, 122. This allows to reduce cross-contamination between fluids which may be successively handled in the device.

In the embodiment illustrated on FIG. 2, the pumping unit 16 comprises three piston pumps 160 of the syringe pump type. One piston pump 160 is connected to the main channel 12, one piston pump 160 is connected to the first buffer channel 121, one piston pump 160 is connected to the second buffer channel 122. In embodiments using volumetric pumps 160, such as the embodiment illustrated in FIG. 2, predetermined fluid volumes can be moved. Fractions of the fluid volume displaced between the different channels 12, 121, 122 may thus be adjusted in a relatively straightforward manner using the total volume of multicomponent fluid contained in the channels 12, 121, 122. The pumps 160 are activated and monitored by a control unit 24.

In FIG. 3, the pumping unit 16 comprises two servo pumps 160. Those servo pumps 160 may be gas pumps 160 of the pressure controller type. The pumping unit 16 illustrated on FIG. 3, further comprises a set of gas valves 25 and connectors allowing to connect each channel 12, 121, 122 to each servo pump 160. The servo pumps 160 and, in the case of FIG. 3, the gas valves 25 are controlled by the control unit 24 with a feedback loop activated by sensors 26. In those embodiments, the control unit 24 comprises six sensors 26. The three sensors 26 located closest to the pumping unit 16 are used to avoid injecting fluid into the pumping unit 16. Filters 27 such as hydrophobic filters of pore diameter inferior to 0.2 μm, are set up between these three sensors 26 and the pumping unit 16 to protect the pumping unit 16 from fluids and to avoid dust or other types of contaminations to be injected in the channels 12, 1212, 122 by the gas pumped by the pumping unit 16. The sensors 26 will be described further below. In embodiments using servo pumps 160, such as the embodiment illustrated in FIG. 3, the volumes of fluid moved are controlled by varying pumping time or intensity (i.e. pumping pressure). In these cases, the relative amounts of fluid displaced between channels 12, 121, 122 is controlled by varying the proportions of pumping time and/or intensity. In these cases, the sensors 26 are helpful to avoid excessive total movement of the multicomponent fluid which may result in gas flow at the flow separation point 20 and undesired bubble generation by the simultaneous flow of gas and multicomponent fluid at this point.

In some further embodiments, the pumping unit 16 comprises:

- a peristaltic pump 160 coupled to the device 10 between the flow separation point 20 and the main channel inlet 18*a*, or
- two peristaltic pumps 160, one coupled between each buffer channel inlet 181*a*, 182*a* and the flow separation point 20

In some embodiments, the flow in channels 12, 121, 122 is regulated by valves 28 which are part of the control unit 24. Each valve 28 regulates the flow of one channel 12, 121, 122 and is therefore located between the flow separation point 20 and the inlet of the corresponding channel, preferably close to the flow separation point 20. The valves 28 may cooperate with the pumping unit 16, in particular when the pumping unit 16 allows the application of only one pressure or flow rate at a time, see for example the embodiment of FIG. 3. In this case, the valves 28 enable to select the channels 12, 121, 122, which is subjected to flow. In some embodiments, the valves 28 have a short response time, they are, for example, proportional valves 28. In this case, the valves 28 may be used to modulate the intensity of the flow in the corresponding channel 12, 121, 122. In another embodiment, the valves 28 may be of the pinch-valve type. In this case, the corresponding channel 12, 122, 121 or collector 14 segment may be formed by an elastomer tubing segment. Alternatively, the valves 28 may be membrane-based valves actuated by pressure differential, eventually of the microfluidic type. The valves 28 preferably allow an easy replacement of the channels 12, 121, 122 and collector 14.

Regardless of the embodiments, the pumping unit 16 and control unit 24, including sensors 26 and valves 28, allow to move controlled volumes of the multicomponent fluid volume from the first or second buffer channel 121, 122 to the main channel 12 or from the main channel 12 to the first or second buffer channel 121, 122.

The pumping unit 16 and the control unit 24 are thus configured to:

- move the multicomponent fluid from the main channel 12 to the first or the second buffer channels 121, 122 through the collector 14; and move the multicomponent fluid from the first or the second buffer channels 121, 122 to the main channel 12 through the collector 14.

This configuration allows to distribute the content of the main channel 12 successively between several buffer channels 121, 122, where multicomponent fluid is stored temporarily. Then, the same configuration allows to flow simultaneously the contents of the buffer channels 121, 122 into the main channel 12. This set-up allows to split an amount of liquid into two parts, then to fold back one part over the other. Thus, multicomponent fluid is homogenized, under laminar flow conditions, without high shear stress so that dispersed components in the fluid are not damaged.

In some embodiments, the pumping unit 16 further controls the pressure of the multicomponent fluid present in the main channel 12 and in the buffer channels 121, 122 and is preferably connected to the main and/or buffer channels 12, 121, 122 via filters 27 of porosity below 0.2 μm, and made of an hydrophobic filtering medium.

Using relatively high flow rate potentially combined with flow obstacles in the collector 14 volume may provide some vorticial or turbulent flow. Such a flow may increase mixing effects and reduce the required number of homogenization cycles implemented by the device 10 in order to get a satisfying result. Depending on the nature of the multicomponent fluid a laminar microfluidic mixer (not shown) might be needed. Such a mixer might be positioned within the main conduct 19. Such mixing effect occur at a cross section level and not longitudinally, they are therefore complementary to the main principle of the invention.

As aforementioned, the pumping unit 16 may comprise at least one sensor 26 allowing the detection of the presence of fluid, inside one of the channels 12, 121, 122 or the collector 14. In the embodiment of FIG. 3, one sensor 26 is positioned, on the main conduct 19 and each fiber 191, 192, between the flow separation point 20 and each buffer channel 12, 121, 122. Each sensor 26 is able to detect the presence of a fluid inside the fibers 191, 192, the main conduct 19 or each channel 12, 121, 122. Each sensor 26 is able to detect the presence of a fluid inside each fiber 191, 192, the main conduct 19 or each channel 12, 121, 122 without direct contact to the fluid.

In embodiments comprising one or several purge outlets 23, a sensor 26 is preferably positioned between the flow separation point 20 and each purge outlet 23. This allows to, firstly, pump the multicomponent fluid out of the corresponding channel 12, 121, 122 up to the position of each corresponding sensor 26, then flush the collector 14 and the corresponding channel 12, 121, 122 using the considered purged outlet 23. This way, no volume of multicomponent fluid remains inside the device 10, and this contributes to lower cross-contamination between successive operations.

More precisely, in one embodiment, the sensors 26 are light sensitive sensors and the channels 12, 121, 122, the main conduct 19 and the fibers 191, 192 are made of transparent material. In this embodiment, the sensors 26 comprise, on a first side of a channel 12, 121, 122, the main conduct 19 or a fiber 191, 192 a set of light sources. On a second face of a channel 12, 121, 122, the main conduct 19 or a fiber 191, 192, the sensors comprise a set of light detectors. The set of light sources faces the set of light detectors. The sensors 26 further comprise electronics controlling the light sources and measuring the light detectors signals. As the light sources emit at a constant rate, the power received by the light detectors is modulated by the presence or absence of multicomponent fluid between the light sources and the light detectors. This allows the multicomponent fluid detection by the sensor 26. The light sources may be electroluminescent diodes emitting in the infrared or visible range and the light detectors are photodiodes. For better accuracy, a sensor 26 can comprise two couples of facing source and detector. This enables to detect at which moment the position of the multicomponent fluid extremity (i.e. meniscus) is located between the two couples. This type of sensor, illustrated in FIG. 3, allows the pumping unit 16 and control unit 24 to precisely know the position of the multicomponent fluid extremity and enables the pumping unit 16 and the control unit 24 to monitor and move the multicomponent fluid in a very accurate and precise fashion. This allows an increase of the accuracy of flow operations, in particular when the device 10 comprises no volumetric pump 160.

In another embodiments, the sensors 26 may comprise an acoustic source and an acoustic detector, or a high frequency electromagnetic source and an antenna.

Each sensor 26 is either situated on a fiber 191, 192 or the main conduct 19 at a distance inferior to 20 cm from flow separation point 20, more preferably at a distance inferior to 10 cm from the flow separation point 20, or situated around the inlets 18*a*, 181*a*, 182*a* of the channels 12, 121, 122. More precisely, the sensors 26 situated on the fibers 191, 192 or the main conduct 19 are situated at the junction between the collector 14 and the fibers/main conduct 19, 191, 192.

In some embodiments, to reduce the residual volume $V_R$, a filling fluid is present in parts of the device 10 unoccupied by the multicomponent fluid. This filling fluid is separated from the multicomponent fluid by an interface to avoid mixing. This interface may, for example, be the gas-liquid interface if the driving fluid is a gas. In the embodiment shown in FIG. 3, this filling fluid is a gas which is also used to pump the multicomponent fluid. Sensors 26 allow stopping the pumping at collector 14 limits which avoids the mixing of the filling fluid and the multicomponent fluid by coextrusion at the flow separation point 20. In those embodiments, sensors 26 located near the flow separation point 20 define the collector 14 volume to a minimal value while increasing the device 10 reliability.

In some embodiments, the device 10 enables the maintenance or control of the temperature inside the channels 12, 121, 122, the main conduct 19, the fibers 191, 192 and the collector 14.

Exchange Functionalities

Thanks to the device disclosed hereabove, multicomponent fluids are handled very easily, yielding well homogenized fluids. In some embodiments, at least one of the main channel (12), first or second buffer channels (121, 122) is further configured to ensure some exchanges between the fluid and an external reservoir. Exchanges may be gas exchanges or solvent exchanges—equivalent to washing—or heat exchanges or energy exchanges—other than heat, for instance light radiation—or chemical exchanges. The combination of exchanges with homogenization leads to very efficient, quick and homogeneous control of multicomponent fluid properties.

Figure 6:
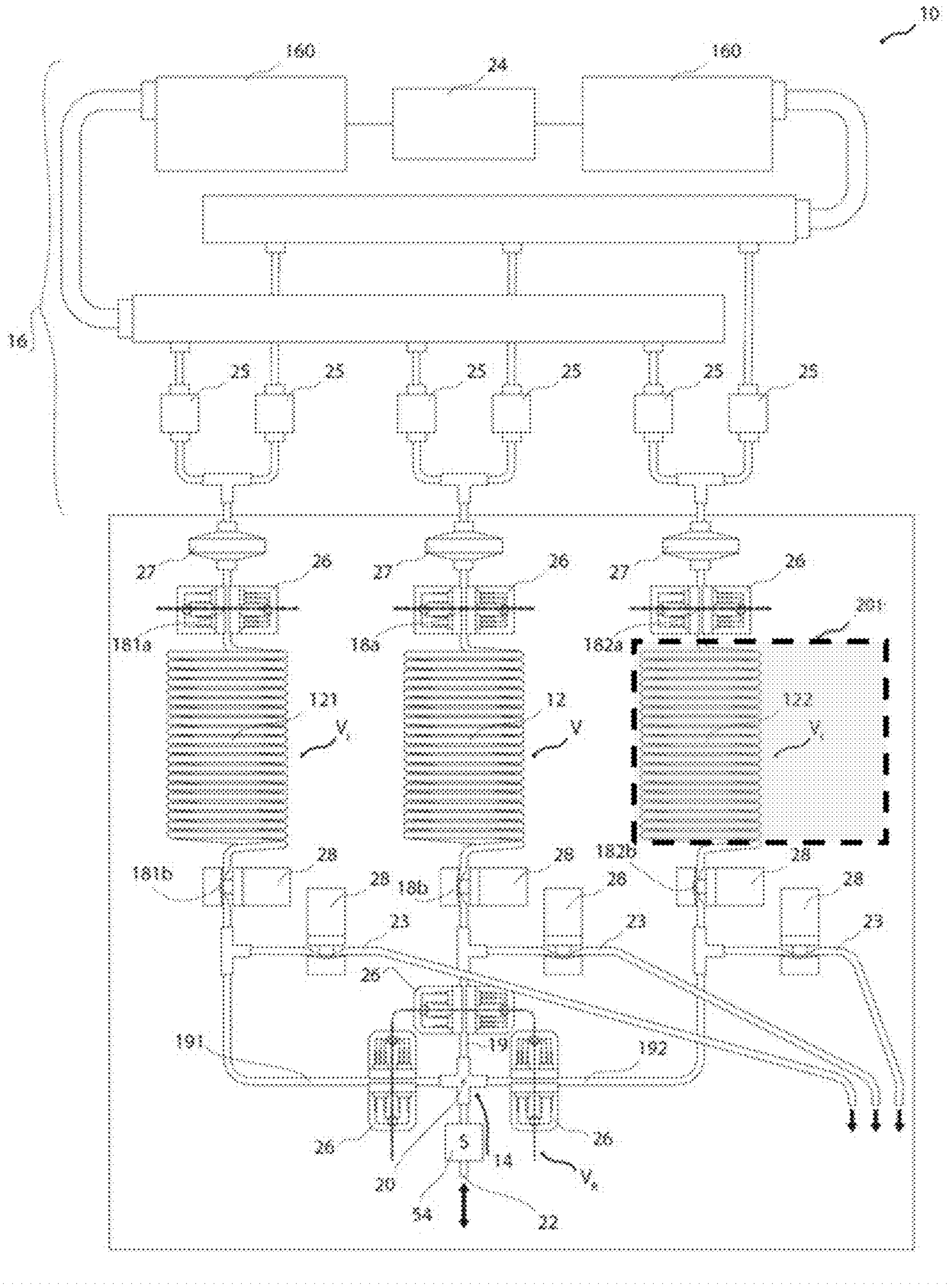
FIG. 6 is a schematic cross-sectional view of an embodiment of the device according to the invention and configured to exchange gas between the multicomponent fluid and an external reservoir.

In some embodiments, at least one of the main channel (12), first or second buffer channels (121, 122) is configured to ensure gas exchanges between the multicomponent fluid and an external reservoir. To this end, a part of the main channel (12), first or second buffer channels (121, 122) may be made of a gas permeable material and enclosed in a cavity comprising a controlled gaseous composition. This gaseous composition may comprise dioxygen, carbon dioxide, water and/or other compounds of interest for the multicomponent fluid. The concentration of all compounds in the cavity is controlled by means well known in the art. FIG. 6 illustrates this embodiment: second buffer channel (122) is made of a gas permeable material and enclosed in a cartridge (201) whose content is a gas with controlled humidity. In this configuration where first buffer channel (121) is helicoidal with a large external surface, gas exchanges—proportional to exchange surface—is large and enables quick diffusion of gas from cartridge (201) into multicomponent fluid.

Figure 7:
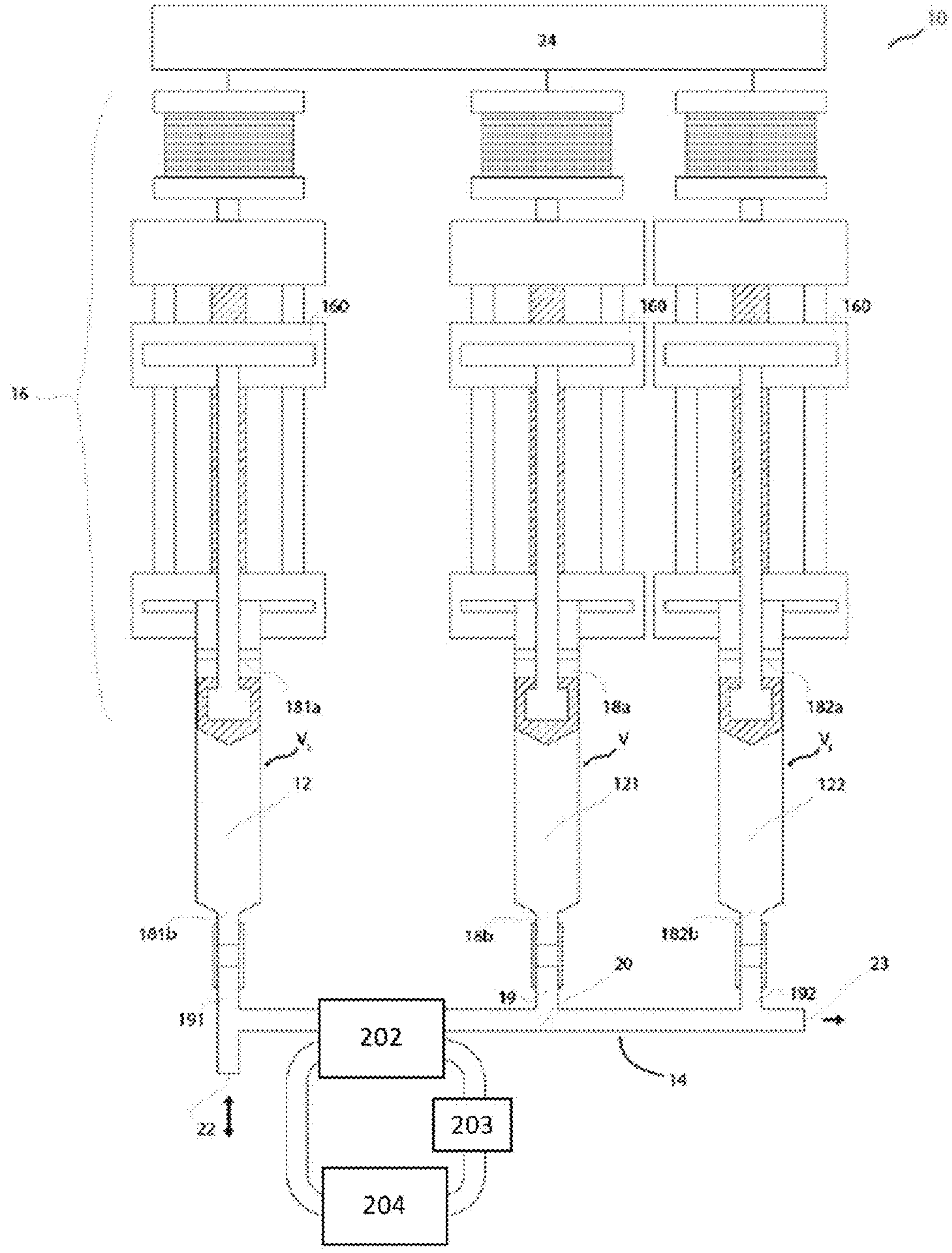
FIG. 7 is a schematic cross-sectional view of an embodiment of the device according to the invention and comprising an exchange cell configured to exchange solvent between the multicomponent fluid and an external reservoir.

In some embodiments, at least one of the main channel (12), first or second buffer channels (121, 122) is configured to ensure solvent exchanges between the multicomponent fluid and an external reservoir. To this end, an exchange cell (202) may be laid on the main channel (12), first or second buffer channels (121, 122). This exchange cell allows for solvent exchange but not for the transfer of particles dispersed in the multicomponent fluid. Such exchange cells may use microporous structures—such as membrane contactor sold by 3M under the Liqui-Cel™ series—or filtering means such as dead end filtration, tangential filtration, cross-flow filtration, sedimentation based filtration, acoustophoretic filtration, electrophoretic filtration, dielectrophoretic filtration, photophoretic filtration, deterministic lateral displacement filtration, flow effect filtration (e.g. flow focusing, Segré-Silberberg effect), counterflow filtration, centrifugation, or any other. FIG. 7 illustrates this embodiment, in which a fluid is circulated by a pump (203) from a reservoir (204) to an exchange cell (202) allowing solvent exchange—but not particle exchange—with the multicomponent fluid contained. The solvent may be pure so that solvent exchange results in cleaning of multicomponent fluid. The solvent may contain culture compounds (nutrients for cells, salts In a particular embodiment of solvent exchange, multicomponent fluid may be concentrated by extraction of solvent through the exchange cell.

In a particular embodiment of solvent exchange, the exchange cell may be configured to sort particles so as to remove from multicomponent fluid particles having specific properties such as size, surface chemistry, optical features . . . .

In some embodiments, at least one of the main channel (12), first or second buffer channels (121, 122) is configured to ensure heat exchanges between the multicomponent fluid and an external heat source or sink. To this end, a part of the main channel (12), first or second buffer channels (121, 122) may be made of good thermal conductor and disposed in contact with a heat source or sink, preferably, having a high thermal inertia. The combination of homogenization properties of the device (10) with heat exchange allows to quickly and homogeneously control temperature of the whole multicomponent fluid handled in the device (10).

In some embodiments, at least one of the main channel (12), first or second buffer channels (121, 122) is configured to ensure energy exchanges other than heat—actinic radiation and/or light in the range of 280 nm to 3000 nm—between the multicomponent fluid and an external source. To this end, a part of the main channel (12), first or second buffer channels (121, 122) may be made permeable to energy, in particular transparent to light. In order to optimize energy transfer from the source to the multicomponent fluid, and in particular to the particles, waveguides, reflectors and/or light scatterers may be used.

Figure 8:
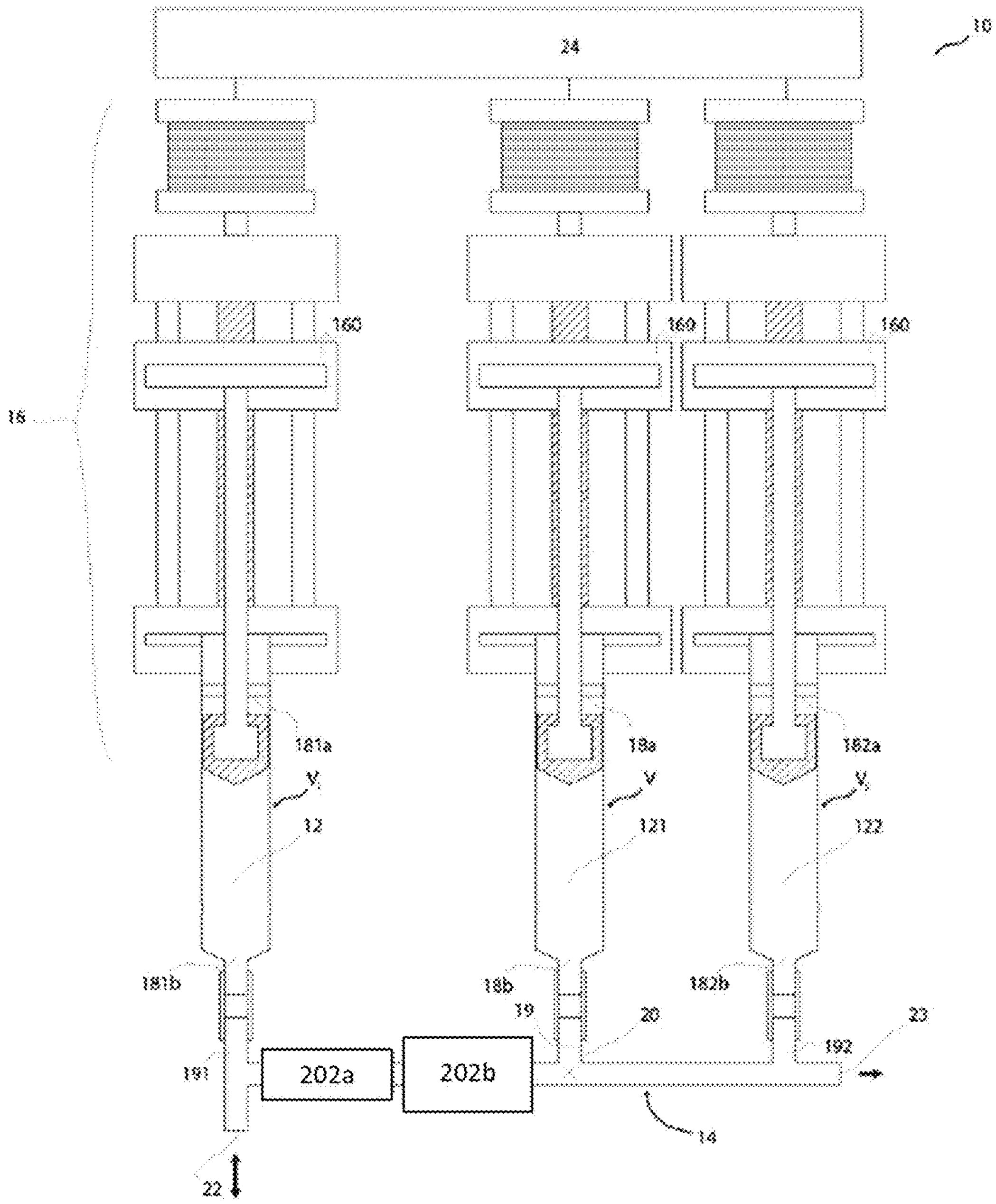
FIG. 8 is a schematic cross-sectional view of an embodiment of the device according to the invention and configured to exchange chemical compounds between the multicomponent fluid and an external reservoir.

In some embodiments, at least one of the main channel (12), first or second buffer channels (121, 122) is configured to ensure exchanges of chemical compounds between the multicomponent fluid and an external reservoir. This embodiment is especially adapted to cell culture—particles of the multicomponent fluid are cells—in which genetic material is directed to cells through their membrane. To this end, an exchange cell (202) may be laid on the main channel (12), first or second buffer channels (121, 122). This exchange cell may implement techniques known in the art such as transmembrane administration, electroporation or membrane perforation. FIG. 8 illustrates this embodiment, in which the exchange cell comprises a transmembrane administration module (202*a*) and a diafiltration cell (202*b*).

In a particular embodiment, chemical exchange consists in removing bubbles from the multicomponent fluid. To this end, a part of the main channel (12), first or second buffer channels (121, 122) may be designed with a bubble trap. So, bubbles that eventually form during processing of multicomponent fluid—due to mixing conditions, leaks or pressure variation inducing gas bubble nucleation—may be eliminated from the multicomponent fluid.

System

Another aspect of the inventions is a system (6) for processing a multicomponent fluid comprising:

i. at least four bioprocessing microfluidic devices (b);
ii. at least three reservoirs (e) or ports configured to connect a reservoir;
iii. at least one buffer tank (c); and
iv. at least two fluidic connection systems;

wherein the first fluidic connection system comprises valves (d2) and connecting means (d1) between valves (d2), so that each reservoir (e) or port configured to connect a reservoir (e) may be in fluidic connection with each buffer tank (c); and the second fluidic connection system comprises valves (d2) and connecting means (d1) between valves, so that each bioprocessing microfluidic device (b) may be in fluidic connection with each buffer tank (c); and wherein one of the at least one buffer tank (c) is the device (10) for homogenizing a multicomponent fluid disclosed hereabove.

In this aspect of the invention, bioprocessing microfluidic devices (b) comprise at least one chamber, in which a multicomponent fluid may be stored and manipulated; at least one inlet to fill in the chamber and at least one outlet to drain out the chamber.

In this aspect of the invention, reservoirs (e) may be included per se in the system (6), or reservoir (e) may be outside the system (6) but connected to the system (6) through a port.

In this aspect of the invention, buffer tank (c) is controlled by a pressure source (c11). Said pressure source (c11) may produce a high pressure leading to drain the buffer tank (c) out, partially or totally. Said pressure source (c11) may produce a low pressure leading to fill in the buffer tank (c), partially or totally. Thanks to the pressure source (c11) and the first and second fluidic connection systems, flows between components of the system may be all controlled with the pressure source (C11). In a particular embodiment, the system (6) comprises at least two buffer tanks, in particular, two, three, four or five buffer tanks. In addition, one buffer tank (e) is a device (10) for homogenizing a multicomponent fluid disclosed hereabove.

In this aspect of the invention, a valve (d2) is a mean to block or allow a fluid flow. Without limitation, valves may be: septa, swabbable valves (for example as disclosed in U.S. Pat. No. 6,651,956), pinch valves such as pinch valves based on elastomeric tube pinching, pinch valves based on microfluidic channel closure by membrane deformation (for example as disclosed in U.S. Pat. No. 6,929,030), other type of membrane-based valves, phase transition valves such as valves operating by freezing the liquid content of a tube, mechanical valves (e.g. quarter turn stopcock, ball valves), surface tension based valves (e.g. in low pressure applications simply disconnecting two parts constituting the flow path to create an energy barrier due to air-liquid surface energy).

Figure 9:
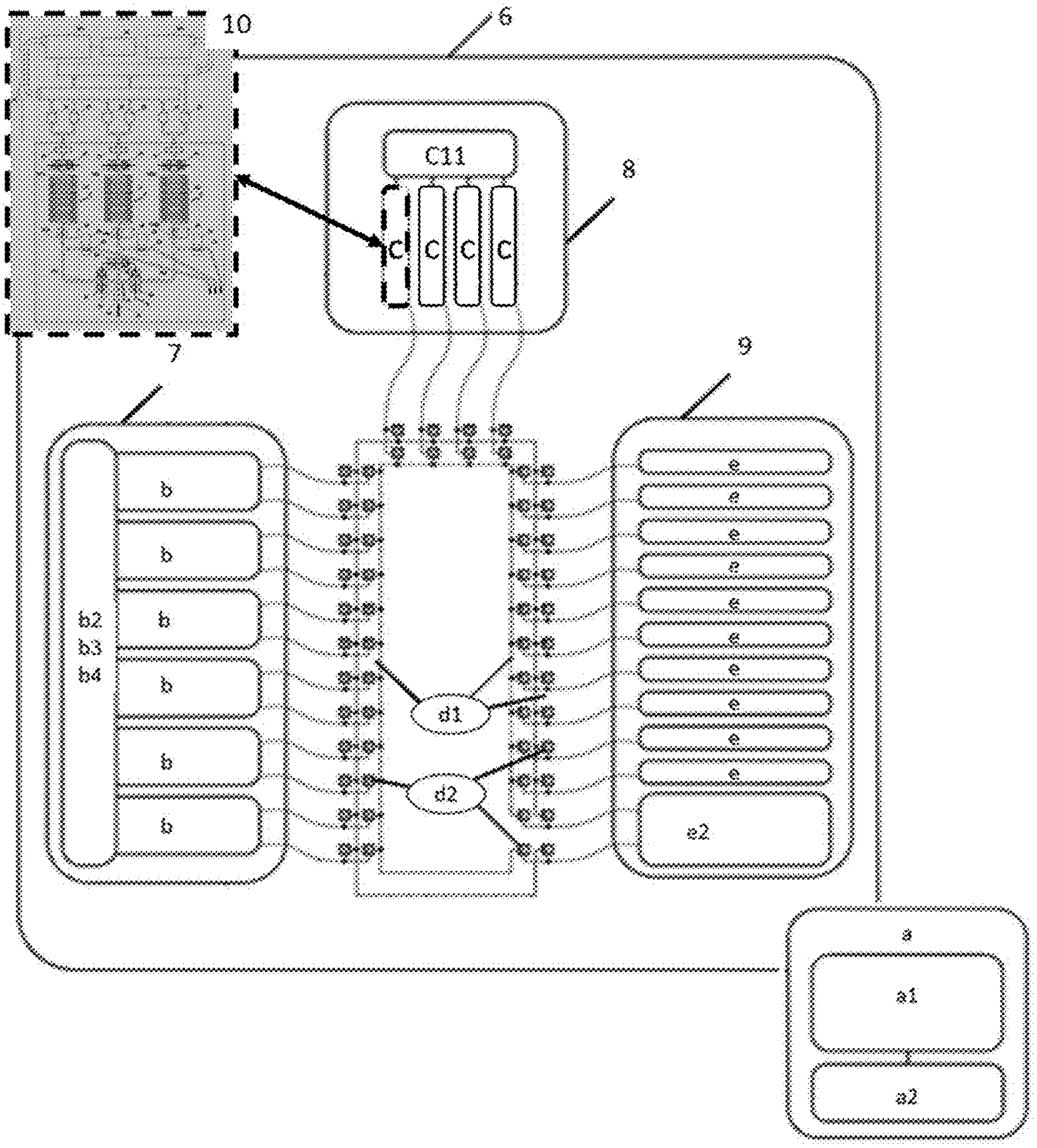
FIG. 9 is a schematic architecture of a system for processing a multicomponent fluid.

In the specific embodiment shown in FIG. 9, six microfluidic devices (b) are placed in a chamber (7) of the system (6). Each microfluidic device comprises an inlet and an outlet (i.e. two ports), both ending with a valve (d2). Ten reservoirs (e) are placed in the system (6) and comprise an outlet ending with a valve (d2). Here, reservoirs (e) are refrigerated in a refrigerated chamber (9). Four buffer tanks (c) are placed in the system (6) and comprise an inlet/outlet ending with a valve (d2). Here, buffer tanks (c) are temperature controlled in a chamber (8), typically at the temperature multicomponent fluid is processed. Between valves (d2) are arranged connecting means (d1) in the form of tubes. By proper configuration of open and closed valves, each reservoir can be in fluidic connection with each buffer tank and each buffer tank can be in fluidic connection with each microfluidic device. Last, one of the four buffer tanks (e) is actually the device (10) disclosed herein (as identified by the arrow on FIG. 9).

Here, the first fluidic connection system comprises valves (d2) associated to reservoirs (e) and buffers tanks (c) and connecting means (d1) between these valves (d2). 28 valves (d2) are used to connect 10 reservoirs (e) with 4 buffer tanks (c). The second fluidic connection system comprises valves (d2) associated to microfluidic devices (b) and buffers tanks (c) and connecting means (d1) between these valves (d2). Valves (d2) associated with buffer tanks (c) are part of both the first and the second fluidic connection systems.

Microfluidic devices (b) are further linked to control modules (b2, b3) for temperature and dissolved gas concentration in chamber (7). Water content of microfluidic devices is further controlled by a module (b4) to measure water loss and eventually add or remove water in microfluidic devices if required. When water loss is caused by evaporation, water vapor is added in the chamber comprising the microfluidic devices (b).

In the example shown in FIG. 9, system (6) comprises a waste tank (e2). In addition, buffer tanks (c) are controlled by a pressure source (c11), here a pressure controller. Last, a controller (a) with a user interface (a1) and a central computer (a2) enables setting flows in the system according to the process considered. The controller monitors parameters: temperature, pressure, humidity, gas concentration in microfluidic devices, water loss of microfluidic devices, time and duration of process steps and defines flows between all components of the system in terms of flow rates and displaced volumes.

With such a system, the first and second fluidic connection systems allow for improved versatility in bioprocess management. Indeed, all reactants may be distributed in each microfluidic device in a controlled manner, with reduced size and dead portions of connecting means and distributing means. Within this disclosure, a dead portion relates to a volume of connecting means that has to be filled or flushed with a liquid during flow in or from a component, i.e., microfluidic device, buffer tank or reservoir, said liquid being staying outside components and being lost in translation. Last, the combination with the device for homogenizing multicomponent fluid being used as a buffer tank allows to ensure mixing during fluid transfers.

Method

The device 10 aims at implementing a method for homogenizing a multicomponent fluid, in particular a cell suspension.

This method comprises following steps:

a. defining a homogenizing parameter n, which is an integer larger than or equal to 2;
b. providing the device 10 with a main channel 12, n buffer channels 121, 122 and a collector 14 connected to the main channel and each of the n buffer channels 121, 122, a pumping unit 16,
c. filling the collector 14 and the main channel 12 at least partially with a volume V of a multicomponent fluid,
d. flowing successively, through the flow separation point 20 of the collector, a fraction $V_i$ of the volume V of the multicomponent fluid from the main channel 12 to each buffer channels 121, 122 in such a way that, after step d is finished, the portion of the residual fluid volume $V_R$ situated upstream the flow separation point 20 is inferior to 20% of the volume V; and
e. flowing simultaneously the multicomponent fluid fraction volume $V_i$ from all buffer channels 121, 122 to the main channel 12.

In another embodiment of the method, the residual fluid volume $V_R$ situated upstream the flow separation point 20 is inferior o 10% of the volume V. In a further embodiment of the method, the residual fluid volume $V_R$ situated upstream the flow separation point 20 is inferior of 5% of the volume V.

The fractional volumes $V_i$ may all be equal but they may also differ for each buffer channel. The residual fluid volume is thus calculated as $$V_R = V - \sum_{i=1}^{n} V_i.$$

In case the fractional volume $V_i$ is the same for each buffer, $V_R=V-nV_i$. The volume of multicomponent fluid hat is actually flown towards the buffer channels and thus homogenized is $$\sum_{i=1}^{n} V_i = V_P.$$

The volume $V_P$ of the multicomponent fluid is thus defined as the total volume of multicomponent fluid flown through the separation point 20 towards the buffer channels during the homogenization steps and is therefore the "processed" volume of multicomponent fluid. As can be seen on FIG. 4, effective homogenization is thus solely obtained for $V_P$, the part of volume V which is flown through the flow separation point 20 during the homogenization steps, whereas the fraction of the fluid not flowing through this point, $V_R$, remains unblown and thus unhomogenized.

Figure 4:
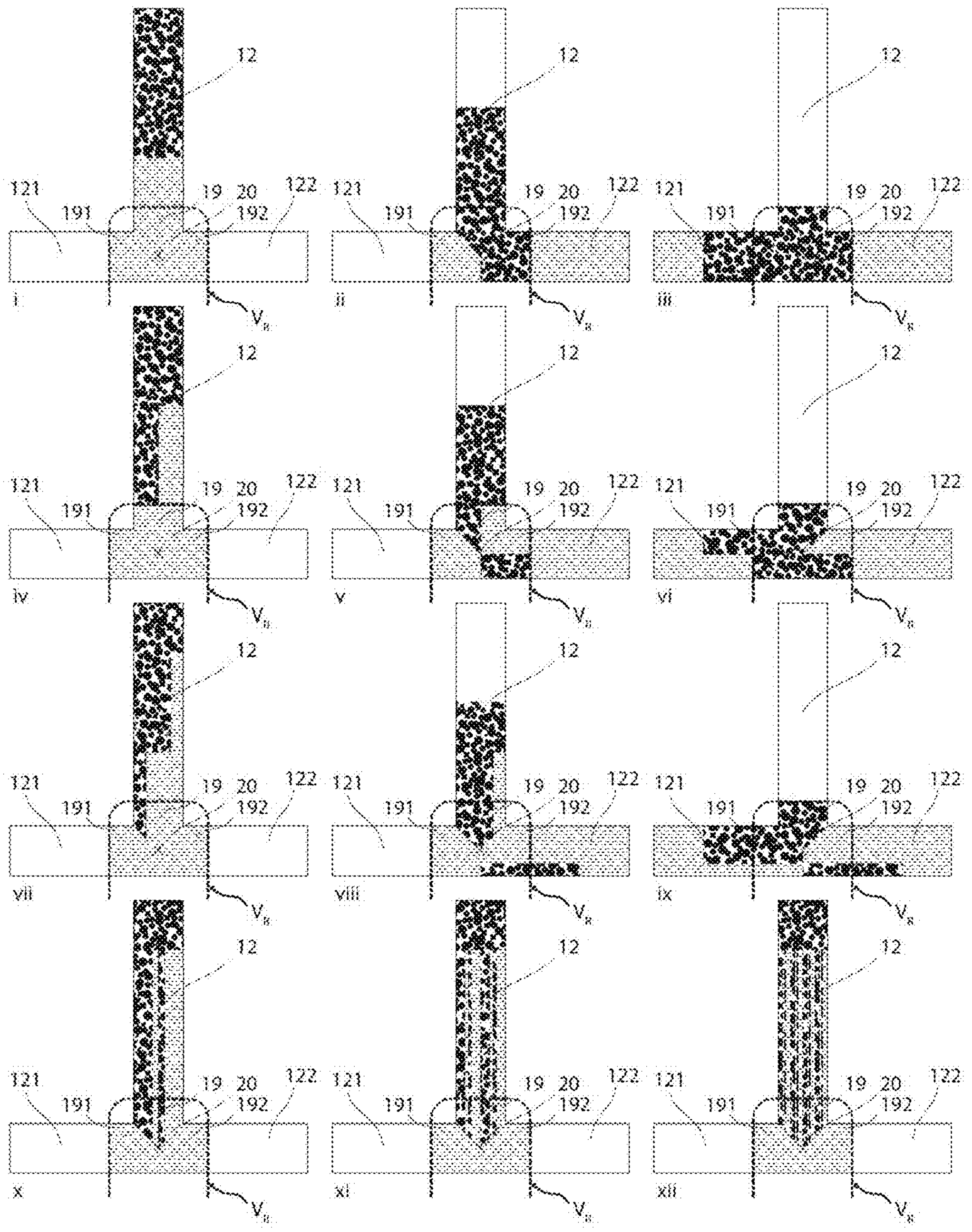
FIG. 4 is a schematic time point view of the method according to the present invention.

As is visible in FIG. 4, the residual volume $V_R$ has a great impact on the performance of the device 10. In the illustrated case, $V_R$ results in a fraction of the multicomponent fluid which is never mixed and is, as such, not usable for high precision dosing. Because the fraction of each component of the fluid in $V_P$ or $V_R$ may not be controlled, this may further affect the concentration of the components of the multicomponent fluid within the processed volume $V_P$, and change it with regards to the initial concentration within the total volume V, and as a result this may affect the achievable dosing accuracy.

In some embodiments, like the embodiment illustrated on FIG. 2, when an adequate filling procedure is used, the device 10 is filled with the multicomponent fluid in such a way that the volume V of multicomponent fluid does not contain empty or gas volumes except gas volumes which may be part of the composition of the multicomponent fluid.

In such cases, as already mentioned, the collector 14 and the residual volume $V_R$ are defined by the pumping limits of the pumping unit 16. In the particular case of the embodiment of FIG. 2, these volumes correspond to the inner volume which can be swiped by the syringe pump piston-gasket assembly.

In other embodiments, to further reduce the residual volume $V_R$, a filling fluid is present in parts of the device unoccupied by the multicomponent fluid. This filling fluid is separated from the multicomponent fluid by an interface to avoid mixing. This interface may for example be the gas-liquid interface if the driving fluid is a gas. In the embodiment shown in FIG. 3, this filling fluid is a gas which is also used to pump the multicomponent fluid. Sensors 26 allow stopping the pumping at collector 14 limits which avoids the mixing of the filling fluid and the multicomponent fluid by coextrusion at the flow separation point 20. In those embodiments, sensors 26 located near the flow separation point 20 define the collector 14 volume to a minimal value while increasing the device 10 reliability.

Actually, the homogenization process induces fluidic exchanges (for example and among others, due to the flow profile and diffusion effects), thus introducing interactions between $V_P$ and $V_R$ affecting the extremities of the processed volume $V_P$ near the residual volume fractions YR. For this reason, it is advantageous, when steps d and e are repeated, to change the order in which the buffer channels 121, 122 are filled with the multicomponent fluid. In this way, the interactions between $V_P$ and $V_R$ are somehow averaged over the processed volume $V_P$.

In the embodiments illustrated on FIGS. 1, 2, and 3, n equals 2 and the homogenized volume $V_P$ of multicomponent fluid is flown in two buffer channels 121, 122.

During step d, the volume V of multicomponent fluid is separated into several volume fractions $V_i$ between the different buffer channels 121, 122 by successive flow operations. It is to be noted, that a residual volume $V_R$ remains unhomogenized, as can be seen on FIG. 4. During step e, the several volume fractions $V_i$ of multicomponent fluid are merged together and refilled simultaneously to the main channel 12. This way, the volume fractions $V_i$ transferred to the buffer channels 121, 122 become elongated by a factor equivalent to the number of buffer channels if all channels are simultaneously coextruded. In the case illustrated on FIGS. 1, 2 3 and 4, the buffer channels 121, 122 represent roughly two halves of the total volume V of multicomponent fluid along its longitudinal axis thus, both volume fractions $V_i$ being equal, the volume V of multicomponent fluid becomes elongated by a factor two. while joined together by the coextrusion flow occurring in step e.

FIG. 4 illustrates successive time points i, ii, iii, iv, v, vi, vii, viii, ix, x, xi, xii, of a multicomponent fluid homogenization method according to the invention, in a chronological order, with n equals 2. To represent the multicomponent fluid heterogeneity, it has been represented using two different fillings. At time point i, the multicomponent fluid occupies the volume V and part of it has been arbitrarily filled with a darker visual texture in order to enable visualization of the homogenization. The time point i of FIG. 4 represents the initial situation of step d. The time points ii and iii represent the result after the first and the second flows of step d. The time point iv represents the result after the step e, i.e. after one mixing cycle. The time points v and vi of depict the result of the first and second flow with a repetition of step d, and time point vii shows the result after a third repetition of step e. Similarly, time points vii, viii and ix depict the successive states of a fourth cycle of repetition of steps d and e. Time points x shows the result after one more cycle of steps d and e, time point xi shows the result after a sixth repetition of steps d and e and time point xii illustrates the homogenization result of the multicomponent fluid after the seventh and last repetition of steps d and e.

With every cycle of repetition of steps d and e during the homogenization process, the properties of the processed volume $V_P$ of multicomponent fluid measured at a cross-section located within the processed portion $V_P$, appear to be the average of the multicomponent fluid properties of two distant cross-sections of the processed portion $V_P$ prior to this cycle. This is particularly easy to visualize between time points x and xi and between time points xi and xii of FIG. 4.

Hence a normalized longitudinal coordinate X can be defined. This normalized longitudinal coordinate X ranges from 0 to 1, of the processed portion $V_P$ of the multicomponent fluid after each step e termination. A value of X thus unequivocally defines a cross section of the processed portion $V_P$ of the multicomponent fluid, and the properties of a cross-section of the multicomponent fluid at coordinate X after one cycle of steps d and e, are the average properties of the multicomponent fluid prior to this cycle, taken at the cross sections located at X/2 and X/2+0.5

After a number m of repetitions of steps d and e, the properties of the multicomponent fluid at a cross-section X are the average properties of the multicomponent fluid prior to these cycles at the cross sections located at each position of this set:

$$\left\{\frac{X}{2^m}+\frac{i}{2^m};\, i\in\{0\ldots\, 2^m-1\}\right\}$$

Hence at the cross-section X, after m cycles, the properties of the multicomponent fluid are an average of the properties of the multicomponent fluid prior to the mixing cycles at $2^m$ positions uniformly distributed along X, i.e. uniformly distributed in $V_P$. In other words, the repetition of cycles d and e exponentially increases the averaging sample size of the fluid properties over the processed volume $V_P$ in an uniform manner, virtually guaranteeing near perfect homogeneity for reasonably small number of m.

Figure 5:
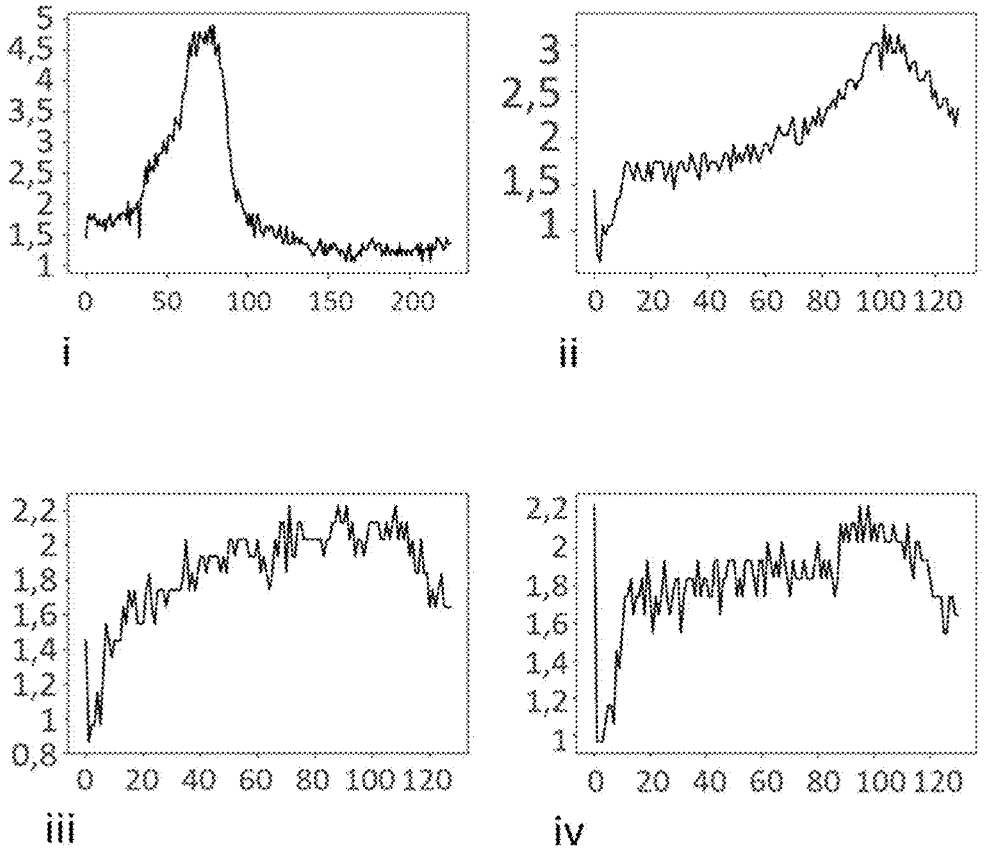
FIG. 5 is a series of experimental graphs graduated in Millions cells/mL (Y-axis) per seconds (X-axis)

FIGS. 5*i* to 5*iv* illustrate an example of multicomponent fluid homogenization. This example is about a cell culture in suspension within a saline solution. The measures have been taken by means of an absorbance captor situated inside the main conduct 19 at a constant flow rate. FIG. 5*i* depicts the initial multicomponent fluid, before the homogenization process has started. On the abscissa axis, the time is indicated in seconds. The fluid flowing through the captor displays an important inhomogeneity with a cell concentration peak of 5 Mø/mL (Millions of cells per milliliter) flowing through the captor around 60-70 seconds and an average cell concentration of 1.2 Mø/mL during the rest of the measuring time. FIG. 5*ii* illustrates the same multicomponent fluid after a first implementation of steps d and e of the method. The cell concentration oscillates between 1.5 and 3 Mø/mL during all the measure time. FIG. 5*iii* illustrates the same multicomponent fluid after a second implementation of steps d and e of the method. The cell concentration oscillates between 1.6 and 2.2 M/mL during all the measure time. FIG. 5*iv* illustrates the same multicomponent fluid after a third implementation of steps d and e of the method. The cell concentration oscillates between 1.8 and 2.2 MØ/mL during all the measure time. The method according the present invention achieves thus a good homogenization of the cell suspension. It can be noted in FIGS. 5*ii* to 5*iv* that initial values of cell concentration of the suspension remain low and doesn't average as the remaining of the suspension profile, this is due to the fact that the part of the fluid monitored on the left most part of the suspension profile in 5*ii* to 5*iv* belongs to $V_R$.

In cases where n is greater than 2, it is advantageous to arrange, regarding the flow separation point 20, each buffer channel identically. It is especially advantageous if the volume of the fibers 191, 192 leading to each buffer channel 121, 122 is designed to be identical. In such preferred cases, the properties at position X after m cycles of steps d and e, is the average of the multicomponent fluid properties prior to these cycles in cross-sections located at:

$$\left\{\frac{X}{n^m} + \frac{i}{n^m}; i \in \{0 \ldots n^m - 1\}\right\}$$

The steps d and e might be repeated until the wished level of homogeneity has been reached. In reality, at a certain value of m, depending of the fluid properties and the device 10 dimensions, the dimensions and number of the components of the fluid limit the possibility for further homogenization:

the concentration of a particular type of component is variable at a length scale corresponding to the component size, the total number of a given component in a sub-volume, limits achievable homogeneity due to statistical fluctuations.

This method allows a very efficient and determinist homogenization almost completely independent of the properties of the particles suspended within the multicomponent fluid.

The invention claimed is:

1. A device for homogenizing a multicomponent fluid comprising:

i) a main channel, ii) a first and a second buffer channel, iii) a collector connected to the main channel by means of a main conduct, and connected to the first buffer channel by means of a first fiber and to the second buffer channel by means of a second fiber, said collector further comprising a flow separation point aimed at dividing the main conduct into the first and second fibers, iv) a pumping unit and a control unit configured together to:

move the multicomponent fluid from the main channel to the first or the second buffer channel through the collector, and move the multicomponent fluid from the first or the second buffer channel to the main channel through the collector.

2. The device according to claim 1, wherein the pumping unit and the control unit are configured together to:

distribute the multicomponent fluid from the main channel successively to the first then to the second buffer channels through the collector, and move the multicomponent fluid from the first and the second buffer channels simultaneously to the main channel through the collector.

3. The device according to claim 1, further comprising at least one sensor allowing a detection of fluid, inside one of the channels, the main conduct, the fibers or the collector.

4. The device according to claim 3, wherein said at least one sensor is able to detect the presence of a fluid without direct contact to the fluid.

5. The device according to claim 3, wherein the pumping unit comprises at least one servo pump being controlled with a feedback loop activated by the at least one sensor.

6. The device according to claim 1, wherein one sensor is positioned, on each fiber, between the flow separation point and each buffer channel.

7. The device according to claim 6, wherein each sensor situated fiber is situated at a distance inferior to 20 cm from flow separation point.

8. The device according to claim 1, wherein the pumping unit comprises at least one volumetric pump in order to move the multicomponent fluid volume from the first or second buffer channels to the main channel or from the main channel to the first or second buffer channels.

9. A method for homogenizing a multicomponent fluid comprising:

a) defining a homogenizing parameter n, which is an integer larger than or equal to 2;

b) providing a device comprising:

i) main channel, ii) n buffer channels, iii) a collector connected to the main channel by means of a main conduct, and connected to each of the n buffer channels by means of a fiber, said collector further comprising a flow separation point aimed at dividing the main conduct into at least two subsets of the n fibers; and iv) a pumping unit configured to move the multicomponent fluid from the main channel to the buffer channels through the collector, or move the multicomponent fluid from the buffer channels to the main channel through the collector, c) filling the collector and the main channel at least partially with a volume of multicomponent fluid, d) flowing successively, through the flow separation point of the collector, a fraction of the volume of the multicomponent fluid from the main channel to each buffer channel in such a way that, after step d is finished, a portion of residual multicomponent fluid volume situated upstream of the flow separation point is inferior to 20% of the volume, and e) flowing simultaneously the multicomponent fluid from all buffer channels to the main channel.

10. The method according to claim 9, wherein the fraction of the volume of multicomponent fluid which is successively flown to the buffer channels equals to 1/n.

11. The method according to claim 9, wherein the portion of residual multicomponent fluid volume situated upstream of the flow separation point is inferior to 10% of the volume.

12. The method according to claim 9, wherein the portion of residual multicomponent fluid volume situated upstream of the flow separation point is inferior to 5% of the volume.

13. The method according to claim 9, wherein steps d and e are repeated at least twice.

14. The method according to claim 13, wherein each time step d is repeated, a filling order of volume of the buffer channels or the fraction of volume flown in the buffer channels is modified.

* * * * *